United States Patent [19]

Cooper et al.

[11] 4,154,757

[45] May 15, 1979

[54] PROCESS FOR THE MANUFACTURE OF p-HYDROXYBENZYL CYANIDE

[75] Inventors: Michael J. Cooper; Philip N. Edwards; Robert J. Copeland, all of Macclesfield, England

[73] Assignee: Imperial Chemical Industries Limited, London, England

[21] Appl. No.: 908,463

[22] Filed: May 22, 1978

[51] Int. Cl.$^2$ .................. C07C 120/00; C07C 121/66
[52] U.S. Cl. ............................. 260/465 F; 260/559 R
[58] Field of Search ..................................... 260/465 F

[56] References Cited

U.S. PATENT DOCUMENTS 3,983,151  9/1976  Meyer ............................. 260/465 F
3,983,160  9/1976  Meyer ............................. 260/465 F

OTHER PUBLICATIONS

C.A., 82, (1975), Hayashi et al., 124965f.
C.A., 85, (1976), Schwartz et al., 46160k.
C.A., 85, (1976), Meyer, 46229q.

*Primary Examiner*—Joseph Paul Brust
*Attorney, Agent, or Firm*—Cushman, Darby & Cushman

[57] ABSTRACT

A process for the manufacture of p-hydroxybenzyl cyanide which comprises reacting p-hydroxymandelic acid with cyanide ion. The product is a useful intermediate for the preparation of the β-adrenergic blocking agent atenolol.

12 Claims, No Drawings

PROCESS FOR THE MANUFACTURE OF P-HYDROXYBENZYL CYANIDE

This invention relates to a new chemical process for the manufacture of the compound p-hydroxybenzyl cyanide, which is a valuable chemical intermediate.

According to the invention there is provided a process for the manufacture of p-hydroxybenzyl cyanide which comprises reacting p-hydroxymandelic acid [α-hydroxy-α-(p-hydroxyphenyl)acetic acid] with cyanide ion.

The cyanide ion is conveniently provided in the form of an alkali metal cyanide, for example sodium or potassium cyanide.

The reaction is conveniently carried out in a relatively high-boiling, dipolar, aprotic solvent, for example N,N-dimethylformamide, 2-pyrrolidone, N-methyl-2-pyrrolidone or dimethyl sulphoxide. Alternatively, a lower-boiling solvent may be used, for example methanol or a mixture of methanol and 1,2-dimethoxyethane, in which case the reaction is preferably carried out in the presence of a formate ester, for example methyl formate. If a high-boiling solvent is used, the reaction is conveniently carried out at a temperature of between 120° and 190° C., for example at about 135° C. If a lower-boiling solvent is used, the reaction is conveniently carried out at the boiling point of the solvent.

The reaction may also optionally be carried out in the presence of a base, for example an alkali metal hydroxide or carbonate, for example sodium or potassium hydroxide or potassium carbonate. Preferably a hydroxide is used in a high-boiling solvent and a carbonate is used in a low-boiling solvent.

The p-hydroxymandelic acid used as starting material is a known compound, but it is most conveniently obtained in the form of sodium or potassium p-hydroxymandelate monohydrate as described in co-pending Application Ser. No. 908,465. It may be used as the monohydrate, or in an anhydrous form which may conveniently be prepared from the monohydrate by azeotropic removal of the water using toluene or xylene as azeotroping solvent.

As stated above, p-hydroxybenzyl cyanide is a valuable chemical intermediate, and in particular it is a valuable intermediate for use, by hydrolysis, in the preparation of p-hydroxyphenylacetamide, which in turn is a valuable intermediate for the preparation of the β-adrenergic blocking agent p-(2-hydroxy-3-isopropylaminopropoxy)phenylacetamide (atenolol).

The invention is illustrated but not limited by the following Examples:

EXAMPLE 1

Sodium hydroxide (4.0 g.) and sodium cyanide (5.0 g.) are added to a stirred suspension of sodium p-hydroxymandelate monohydrate (19 g. of 89% w/w material, the impurity being sodium chloride) in N,N-dimethylformamide (100 ml.) and the mixture is stirred and heated at 135° C. for 4 hours and then cooled. Formic acid (7.7 ml.) and water (200 ml.) are added and the mixture is extracted twice with methyl isobutyl ketone (100 ml. and 75 ml.). The combined extracts are washed twice with water (40 ml. each time) and are then concentrated by evaporation. There is thus obtained a solution of p-hydroxybenzyl cyanide in methyl isobutyl ketone which is suitable for conversion to p-hydroxyphenylacetamide without further purification.

EXAMPLE 2

A stirred suspension of sodium p-hydroxymandelate monohydrate (50 g. of 77% w/w material, the impurity being sodium chloride) and sodium cyanide (12.5 g.) in N,N-dimethylformamide (67.5 ml.) is heated at 135° C. for 2 hours and then cooled. Water (200 ml.) and formic acid (20 ml.) are added and the mixture is extracted twice with methyl isobutyl ketone (200 ml. and 100 ml.). The combined extracts are washed twice with water (50 ml. each time) and are then concentrated by evaporation. There is thus obtained a solution of p-hydroxybenzyl cyanide in methyl isobutyl ketone which is suitable for conversion to p-hydroxyphenylacetamide without further purification.

EXAMPLE 3

A mixture of sodium p-hydroxymandelate monohydrate (208 g.), sodium cyanide (49 g.), potassium carbonate (69 g.), methyl formate (80 ml.) and methanol (300 ml.) is heated under reflux for 8 hours, the temperature being maintained below 58° C. as methyl formate is consumed in the early stages of the reaction by the dropwise addition of further methyl formate (120 ml.). The mixture is cooled and acidified to pH 4 with concentrated aqueous hydrochloric acid (90 ml.), and water (300 ml.) is added dropwise whilst the mixture is distilled under reduced pressure, until the final volume of the two-layer mixture is 530 ml. The upper organic layer is collected and the lower aqueous layer is extracted twice with methyl isobutyl ketone (80 ml. each time). The extracts and organic layer are combined and the mixture is washed with saturated sodium chloride solution (100 ml.) and then with water (80 ml.). The methyl isobutyl ketone is removed by evaporation and there is thus obtained as residue p-hydroxybenzyl cyanide (120 g.) which is suitable for conversion to p-hydroxyphenylacetamide without further purification.

EXAMPLE 4

Sodium cyanide (25.0 g.) is added to a stirred suspension of anhydrous sodium p-hydroxymandelate (96 g. of 99% w/w material, the impurity being sodium chloride; prepared from 104 g. of monohydrate by azeotropic distillation with 500 ml. of xylene in a Dean and Stark apparatus) in N,N-dimethylformamide (100 ml.), and the mixture is heated at 135° C. for 1 hour and then cooled. Water (170 ml.) and formic acid (38 ml.) are added and the mixture is extracted twice with methyl isobutyl ketone (330 ml. and 170 ml. respectively). The combined extracts are washed twice with water (240 ml. and 180 ml. respectively) and then concentrated by evaporation. There is thus obtained a solution of p-hydroxybenzyl cyanide in methyl isobutyl ketone which is suitable for conversion to p-hydroxyphenylacetamide without further purification.

EXAMPLE 5

The conversion of p-hydroxybenzyl cyanide to p-hydroxyphenylacetamide is illustrated by the following procedure:

The solution of p-hydroxybenzyl cyanide in methyl isobutyl ketone obtained in Example 1 is saturated with dry hydrogen chloride, concentrated aqueous hydrochloric acid (3 ml.) is added and the mixture is stirred at laboratory temperature for 16 hours and then filtered. Aqueous ammonium hydroxide solution is added to the solid product until the pH of the mixture is 7, and the mixture is filtered. There is thus obtained p-hydroxyphenylacetamide in 62% yield based on the sodium p-hydroxymandelate used in Example 1.

Under similar conditions, the process described in Example 2 yields 50% of p-hydroxyphenylacetamide; the process described in Example 3 yields 63% of p-hydroxyphenylacetamide which contains less than 2% w/w of ammonium chloride impurity; and the process described in Example 4 yields 74% of p-hydroxyphenylacetamide.

What we claim is:

1. A process for the manufacture of p-hydroxybenzyl cyanide which comprises reacting sodium or potassium p-hydroxymandelate with an alkali metal cyanide in a solvent at a temperature of up to 190° C.

2. A process as claimed in claim 1 wherein the alkali metal cyanide is sodium cyanide.

3. A process as claimed in claim 1 which is carried out in a dipolar, aprotic solvent at a temperature of between 120° and 190° C.

4. A process as claimed in claim 3 wherein the solvent is N,N-dimethylformamide, 2-pyrrolidone, N-methyl-2-pyrrolidone or dimethyl sulphoxide.

5. A process as claimed in claim 4 which is carried out at a temperature of 135° C.

6. A process as claimed in claim 1 which is carried out in methanol or a mixture of methanol and 1,2-dimethoxyethane as solvent at the boiling point of the solvent and in the presence of a formate ester.

7. A process as claimed in claim 6 wherein the formate ester is methyl formate.

8. A process as claimed in claim 3 which is carried out in the presence of a base.

9. A process as claimed in claim 8 wherein the base is an alkali metal hydroxide.

10. A process as claimed in claim 6 which is carried out in the presence of a base.

11. A process as claimed in claim 10 wherein the reaction is carried out in the presence of an alkali metal carbonate.

12. A process as claimed in claim 1 wherein the sodium or potassium p-hydroxymandelate is in the form of its monohydrate.

* * * * *